US00PP35872P3

(12) United States Plant Patent
Arts

(10) Patent No.: US PP35,872 P3
(45) Date of Patent: Jun. 18, 2024

(54) RASPBERRY PLANT VARIETY NAMED 'ABB 128'

(50) Latin Name: ***Rubus idaeus* L.**
Varietal Denomination: ABB 128

(71) Applicant: Allberry B.V., JJ Hedel (NL)

(72) Inventor: Niels Arts, De Kwakel (NL)

(73) Assignee: Allberry B.V., JJ Hedel (NL)

( * ) Notice: Subject to any disclaimer, the term of this patent is extended or adjusted under 35 U.S.C. 154(b) by 0 days.

(21) Appl. No.: 18/445,157

(22) Filed: May 2, 2023

(65) Prior Publication Data

US 2023/0363300 P1 Nov. 9, 2023

(30) Foreign Application Priority Data

May 4, 2022 (QZ) ..... PBR 20221156

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./203, 204
See application file for complete search history.

(56) References Cited

U.S. PATENT DOCUMENTS

RE46,041 E 6/2016 Smaal et al.

*Primary Examiner* — Susan McCormick Ewoldt
(74) *Attorney, Agent, or Firm* — Plant & Planet Law Firm

(57) ABSTRACT

The new and distinct variety of raspberry plant variety 'ABB 128' is provided. The variety can be distinguished by its outstanding features of vigor, easiness to grow, and productivity.

2 Drawing Sheets

Latin name of the genus and species:
Botanical classification:
a. Genus—*Rubus.*
b. Species—*idaeus* L.
Variety denomination: The new raspberry plant claimed is of the variety denominated 'ABB 128'.

CROSS REFERENCE TO RELATED APPLICATIONS

This application claims the benefit of priority under 35 USC § 119 to Community Plant Variety Office (CPVO) Application No. 20221156 for Community Plant Variety Rights, filed on May 4, 2022, for a raspberry plant with a variety denomination of 'ABB 128', which is herein incorporated by reference in its entirety.

BACKGROUND OF THE INVENTION

Field of the Invention

The present invention relates to a new and distinct variety of raspberry plant, which has been given the variety denomination of 'ABB 128'.

Background of the Related Art

Raspberries are the edible fruit of a multitude of plant species in the genus *Rubus* of the rose family. Most raspberry species are in the subgenus *Idaeobatus*. Raspberry plants are perennial plants with woody stems. Many of the most important modern commercial red raspberry cultivars derive from hybrids between *R. idaeus* and *R. strigosus*. Recent breeding has resulted in cultivars that are thornless and more strongly upright, not needing staking.

Both the red and the black raspberry species have albino like pale-yellow natural or horticultural variants. Fruits from such plants are called golden raspberries or yellow raspberries. Most pale-fruited raspberries commercially sold in the eastern United States are derivatives of red raspberries. Yellow-fruited variants of the black raspberry are sometimes grown in home gardens. Despite their dissimilar appearance, golden raspberries retain the distinctive flavor of their respective red or black species.

An individual raspberry fruit is made up of around 100 drupelets, each of which contains a juicy pulp and a single central seed. A raspberry bush can yield several hundred berries in a year. Unlike blackberries and dewberries, a raspberry has a hollow core once it is removed from the receptacle.

Raspberries are traditionally planted in the winter as dormant canes, but planting plugs produced by tissue culture is also common. Additionally, the long cane production method consists of growing canes for one year in cold climates where the bud break is early, and then transplanting the canes to warmer climates where they quickly flower and can produce an early season crop. A very vigorous crop, raspberries spread well and can be considered invasive, using extended underground shoots (also known as suckers or basal shoots) that can develop roots and individual plants.

Raspberries are a popular fruit that are recognized for their antioxidants, high fiber, and as a good source of vitamin C. Raspberry fruit is typically consumed as fresh fruit, individually quick frozen (IQF) fruit, or in prepared foods, such as purees, juices, jellies, jams, grocery items, baked goods, and snack foods.

Raspberry is an important and valuable commercial fruit crop, widely grown in all temperate regions of the world.

Accordingly, there is a need for new varieties of raspberry plant. In particular, there is a need for improved varieties of raspberry plant that are stable, high yielding, and agronomically sound.

SUMMARY OF THE INVENTION

The present invention relates to a new and distinct variety of raspberry, which has been given the variety denomination of 'ABB 128', and is intended for use as fresh fruit.

The new raspberry variety is a selection resulting from a sexual cross of raspberry plants at De Kwakel, Netherlands in 2011, involving a seed parent known as '210001' (unpatented) and a pollen parent known as 'Advabereen' (U.S. Plant Pat. No. 23,915, re-issued as U.S. Pat. No. 46,041).

The selection was subsequently evaluated for a number of years at Rossum, Netherlands.

Asexual reproduction of the new variety by cutting propagation since 2014 at Rossum, Netherlands has demonstrated that the new variety reproduces true to type with all of the morphological characteristics, as herein described, firmly fixed and retained through successive generations of such asexual propagation.

Selection criteria included strong vigor, easiness to grow, and high productivity.

The following characteristics of the new variety have been repeatedly observed and can be used to distinguish 'ABB 128' as a new and distinct variety of raspberry plant: strong vigor, easy to grow, high productivity.

Plants of the new variety differ from plants of the seed parent '210001' (unpatented) as set forth in Table 1. Plants of the new variety differ from plants of the pollen parent 'Advabereen' in fruit size, fruit shape, and fruit color as set forth in Table 2. It is also more vegetative, naturally branching, has a higher yield, less sensitivity to cold, round fruits, high sugar levels.

TABLE 1

| Similar variety | Characteristics | Similar variety level of expression | Candidate variety level of expression |
|---|---|---|---|
| '210001' | Productivity | High | Medium-High |

TABLE 2

| Similar variety | Characteristics | Similar variety level of expression | Candidate variety level of expression |
|---|---|---|---|
| 'Advabereen' | Fruit size | Medium | Big |
| 'Advabereen' | Fruit shape | Irregular | Nice shape |
| 'Advabereen' | Fruit color | Red | Light red |

BRIEF DESCRIPTION OF THE DRAWINGS

The accompanying photographic illustrations show the typical appearance of the new variety 'ABB 128'. The colors are as nearly true as is reasonably possible in a color representation of this type. Colors in the photographs may differ slightly from the color values cited in the detailed botanical description which accurately describes the colors of the new plant.

DETAILED BOTANICAL DESCRIPTION

Figure 1:
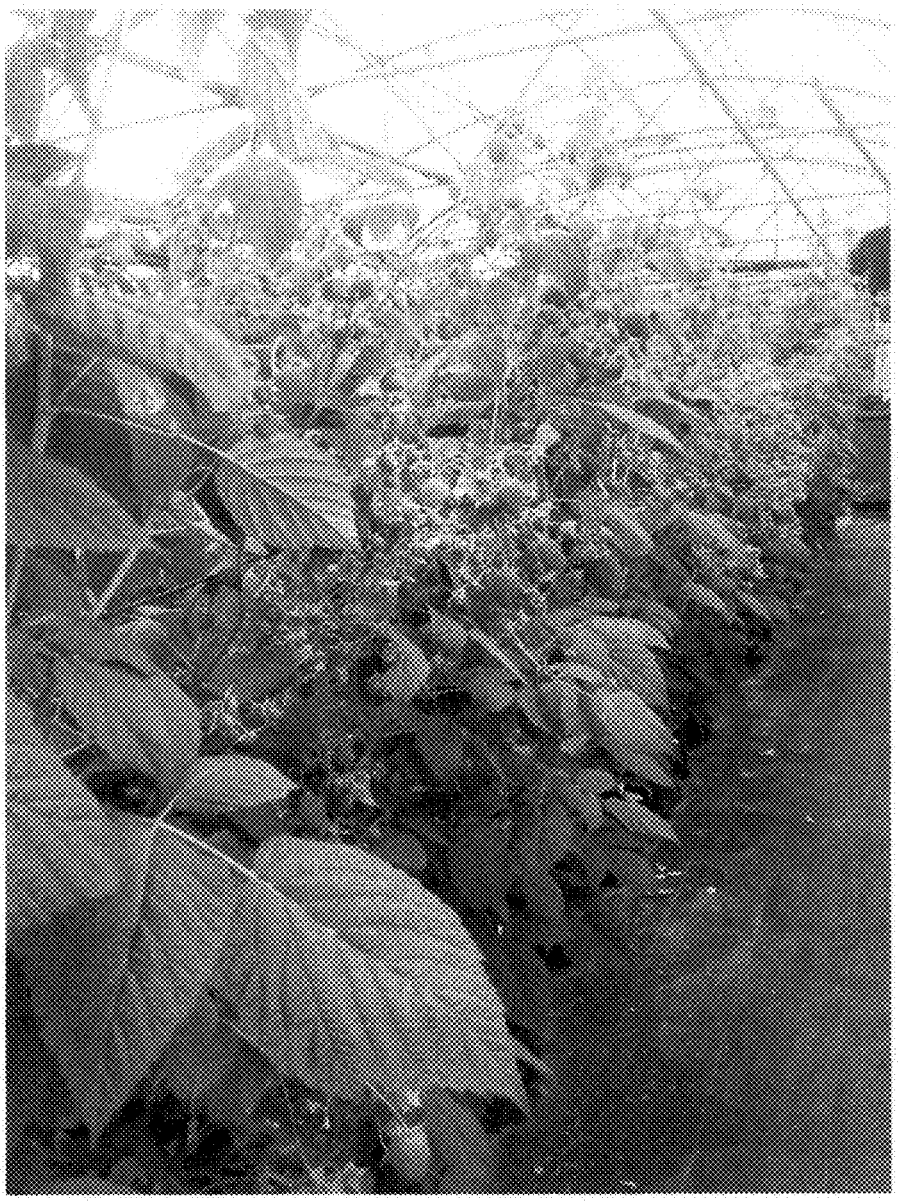
FIG. 1 is a photograph of the new variety 'ABB 128', demonstrating extreme productivity.
Figure 2:
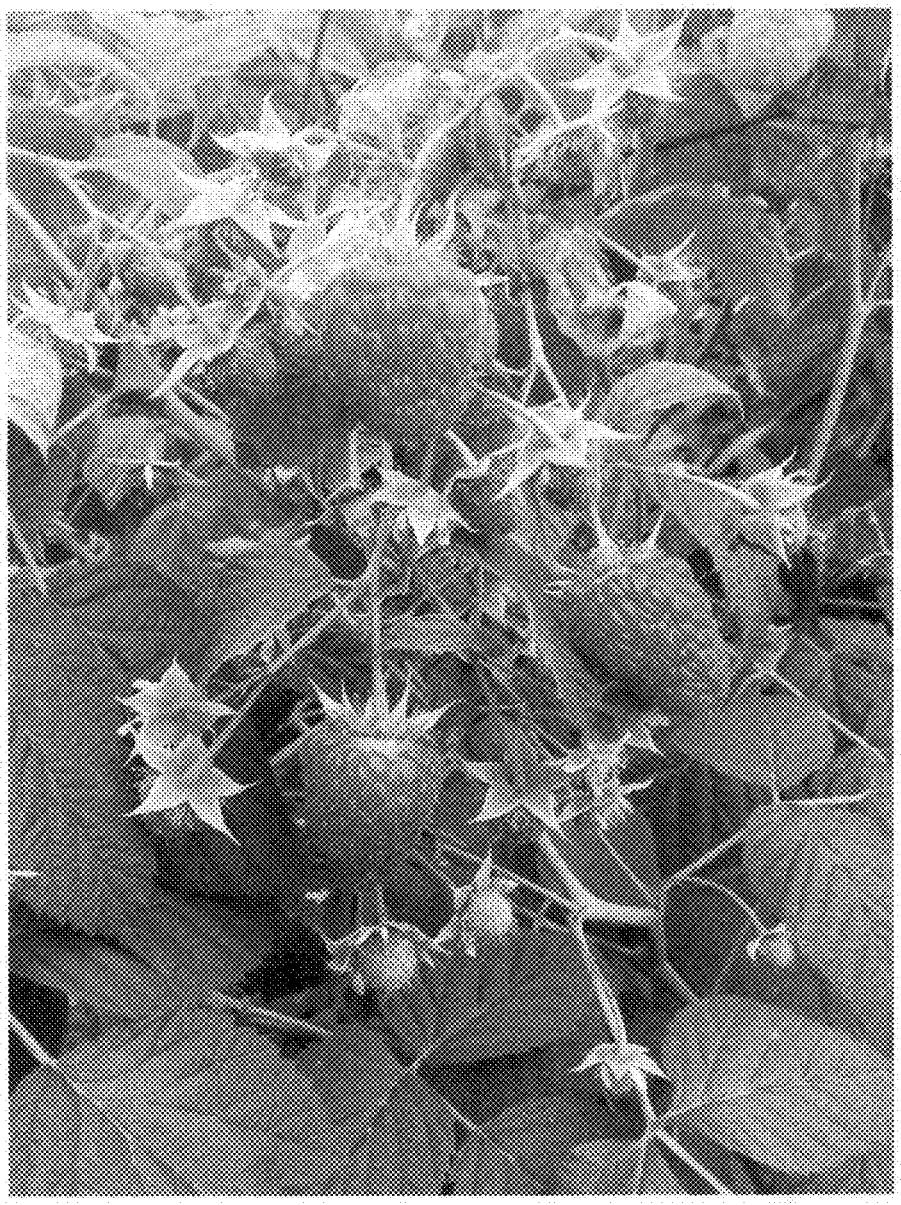
FIG. 2 is a photograph of large fruit of new variety 'ABB 128' at primocane stage.

The following detailed description sets forth the distinctive characteristics of 'ABB 128'. The datum which defines these characteristics was collected from asexual reproductions of the original selection. Dimensions, sizes, colors, and other characteristics are approximations and averages set forth as accurately as possible. The plant history was taken on plants approximately 18 weeks, and the descriptions relate to plants grown in Rossum, Netherlands. Color notations are in reference to the standard R.H.S. Colour Chart 2015.

Classification:

a. *Family*.—Rosaceae.
b. *Botanical*.—*Rubus idaeus* L.
c. *Common name*.—Raspberry.
d. *Variety name*.—'ABB 128'.

Parentage:

a. *Female parent*.—'210001'.
b. *Male parent*.—'Advabereen'.

PLANT

General:

a. *Height*.—200-240 cm.
b. *Width*.—80-100 cm.
c. *Length/width ratio*.—Average.
d. *Growth habit*.—Upright.
e. *Primocane* (*current year's cane*).—i. Color — Green — 135D. ii. Cane length in autumn — 200-240 cm. iii. Internodal distance at central ⅓ of cane — 7 cm. iv. Anthocyanin coloration of cane — Absent. v. Cane bloom — Very strong. vi. Time of cane emergence — Early. 3-4 months. vii. Diameter — 12-25 mm.
f. *Very young shoot*.—i. Anthocyanin coloration of apex during rapid growth — Weak.
g. *Floricane* (*previous year's cane*).—i. Dormant cane color — Brown — 183B. ii. Fruiting lateral attitude — Semi-erect. iii. Fruiting lateral length — 40-50 cm. iv. Diameter — 12-25 mm.
h. *Prickles* (*spines*).—i. Presence — Present. ii. Density — Medium. 3-5 spines per linear cm of cane. iii. Length at 1 inch in height at end of harvest (from base to tip) — Medium. iv. Color — Purplish brown — 59A.
i. *Fruit storage life and shipping quality*.—Good. i. Number of days of storage life at cold temperature — 8-15. ii. Number of days of storage life at room temperature — 4-8. iii. Chilling requirement — Yes.
j. *Market use*.—Fresh fruit.
k. *Plant/fruit disease and pest resistance/susceptibility*.—Low vulnerability for mildew and low vulnerability for spider mites.
l. *Cold/heat tolerance or hardiness zone*.—USDA zones 9-10.

LEAVES

General:

a. *Predominant number of leaflets*.—3.
b. *Profile of leaflets in cross section*.—Straight.
c. *Leaf rugosity*.—Weak.

d. *Color of upper side.—Dark green* — 137A.
e. *Color of lower side.—Light greyish green* — 191A.
f. *Surface texture of upper side*.—Weak rugosity.
g. *Terminal leaflet*.—i. Length — Long. 5-8 cm. ii. Width — Medium. 4-6 cm. iii. Length/width ratio — Medium. iv. Margin — Serrate. v. Overall shape — Rounded oval. vi. Apex shape — Acuminate. vii. Base shape — Elliptical oval.
h. *Lateral leaflets*.—i. Length — Long. 5-8 cm. ii. Width — Medium. 4-6 cm. iii. Length/width ratio — Medium. iv. Relative position of lateral leaflets — Touching. v. Margin — Serrate. vi. Overall shape — Rounded oval. vii. Apex shape — Acuminate. viii. Base shape — Rounded.

FLOWERS

General:
a. *Diameter*.—Medium. 1-2 cm.
b. *Petal*.—i. Length — Medium. 6-10 mm. ii. Width — Medium. 2-3 mm. iii. Length/width — Medium. iv. Color of upper side — 155C. v. Color of lower side — 155C. vi. Number of petals — 5. vii. Margin — Standard. viii. Shape of base — Straight. ix. Shape of apex — Conical. x. Texture — Silky.
c. *Peduncle*.—i. Anthocyanin coloration — Absent. ii. Length — 2-5 cm. iii. Diameter — 0.5-2 mm. iv. Color — Light greyish green — 191A.

FRUIT

General:
a. *Length*.—Long. 25-35 mm.
b. *Diameter*.—Broad. 20-30 mm.
c. *Length/width ratio*.—Medium.
d. *General shape in lateral view*.—Circular to broad conical.
e. *Color*.—Light red — 34A.
f. *Glossiness*.—Strong.
g. *Firmness*.—Strong/firm.
h. *Adherence to plug*.—Medium.
i. *Size of single drupe*.—Small.
j. *Number of drupelets per berry*.—High. 80-150.
k. *Average weight per berry*.—6 grams.
l. *Width*.—2-4 mm.

PRODUCTION

General:
a. *Main bearing type*.—Double crop.
b. *Primocane* (*current year's cane*).—i. Time of beginning of flowering — Early. 16-18 week after planting. ii. Time of beginning of fruit ripening — Medium. 3-4 weeks after flowering. iii. Length of fruiting period — Medium. 6-8 weeks. iv. Yield — High. 20-30 T/Ha.
c. *Floricane* (*previous year's cane*).—i. Time of vegetative bud burst — Medium. 2-4 weeks after cold storage. ii. Time of beginning of flowering — Medium. 8-10 weeks after bud break. iii. Time of beginning of fruit ripening — Early-medium. 3-4 weeks after flowering. iv. Length of fruiting period —0 Medium. 4-6 weeks. v. Yield — High. 20-30 T/Ha.

The invention claimed is:

1. A new and distinct variety of raspberry plant named 'ABB 128', as illustrated and described herein.

* * * * *